US006842796B2

(12) United States Patent
Zweig et al.

(10) Patent No.: US 6,842,796 B2
(45) Date of Patent: Jan. 11, 2005

(54) INFORMATION EXTRACTION FROM DOCUMENTS WITH REGULAR EXPRESSION MATCHING

(75) Inventors: Geoffrey G. Zweig, Greenwich, CT (US); Mukund Padmanabhan, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 329 days.

(21) Appl. No.: 09/898,289

(22) Filed: Jul. 3, 2001

(65) Prior Publication Data

US 2003/0050782 A1 Mar. 13, 2003

(51) Int. Cl.[7] .................................................. G06F 3/00
(52) U.S. Cl. .............................. 710/16; 710/65; 707/1; 707/6; 707/100; 705/1; 705/2
(58) Field of Search .......................... 710/65, 16; 707/1, 707/6, 100; 705/1, 2

(56) References Cited

U.S. PATENT DOCUMENTS

| | | | | |
|---|---|---|---|---|
| 6,002,491 A | * | 12/1999 | Li et al. | ...................... 358/436 |
| 6,317,762 B1 | * | 11/2001 | Okawa et al. | ............... 715/541 |
| 6,342,901 B1 | * | 1/2002 | Adler et al. | ................. 345/700 |
| 2002/0010709 A1 | * | 1/2002 | Culbert et al. | ............... 707/500 |
| 2002/0059266 A1 | * | 5/2002 | I'anson et al. | .............. 707/100 |
| 2002/0194026 A1 | * | 12/2002 | Klein et al. | ..................... 705/2 |

OTHER PUBLICATIONS

Ratnaprkhi, "A Maximum Entropy Part of Speech Tagger," Conference on Empirical Methods in Natural Language Processing, University of Pennsylvania, 1996.
Brill, "Transformation–Based Error–Driven Learning and Natural Language Processing: A Case Study in Part of Speech Tagging," Computational Linguistics, Dec. 1995.

* cited by examiner

Primary Examiner—Jeffrey Gaffin
Assistant Examiner—Justin Knapp
(74) Attorney, Agent, or Firm—Thu Ann Dang; Ryan, Mason & Lewis, LLP (57) ABSTRACT

Techniques are provided for enumerating regularly identifiable or stereotypical phrases that people commonly use to convey particular information, and where exactly in these phrases the particular information is to be found. In one embodiment, such phrases are referred to as "regular expressions." Using such enumerated phrases, the invention is able to automatically identify them in an input data stream and then identify and extract the particular information associated with the phrase that is being sought, e.g., important or relevant information.

25 Claims, 1 Drawing Sheet

INFORMATION EXTRACTION FROM DOCUMENTS WITH REGULAR EXPRESSION MATCHING

FIELD OF THE INVENTION

The present invention relates to data processing techniques and, more particularly, to techniques for providing automatic information extraction from data streams such as text and spoken documents.

BACKGROUND OF THE INVENTION

There are many situations in which it is desirable to extract key pieces of information from documents. For example, in transcribed voice mail messages, the name of the caller and any return numbers that were left are crucial for summarizing the call. Or when resumes are submitted to a company along with a cover letter, it is desirable to extract the job objective and salary requirements of the applicant, in order to determine if a suitable match exists. This invention comprises a simple, efficient, and effective way of extracting such information.

In the past, several techniques have been developed to solve the somewhat simpler problem of "named entity extraction." In this task, the goal is to identify all occurrences of certain classes of words in a document. For example, all the person-names, city-names, dates, and times might be identified. One way of identifying such entities is to train a statistical classification system to tag each word in the document as either a "person-name," "city-name," "date," "time," or "other" word. Examples of this sort of approach are disclosed in, e.g., Ratnaprkhi, "A Maximum Entropy Part of Speech Tagger," Conference on Empirical Methods in Natural Language Processing, University of Pennsylvania, 1996; and Brill, "Transformation-Based Error-Driven Learning and Natural Language Processing: A Case Study in Part of Speech Tagging," Computational Linguistics, December 1995, the disclosures of which are incorporated by reference herein. While the problem of extracting key pieces of information can also be viewed as a tagging problem, in which each word is tagged as either "key information" or "irrelevant," such a tagging approach fails to explicitly identify the portions of text that are important.

Thus, there is a need for data processing techniques which explicitly identify portions of data that are sought to be identified, rather than only implicitly identifying, or tagging, such portions of data.

SUMMARY OF THE INVENTION

The present invention provides techniques for exploiting the readily-identifiable structure of language to explicitly identify portions of data in a document that a user seeks to be identified, e.g., relevant or important information. It is to be understood that the term "document," as used herein in accordance with the invention, is intended to broadly refer to a sequence of symbols (e.g., letters, numbers, characters, etc.), such as a data stream representative of text and/or spoken messages. However, it is to be understood that the invention applies to many input forms other than typed text or spoken messages. By way of further example only, the invention may also be applied to information extraction from data streams representing DNA (deoxyribonucleic acid) sequences, RNA (ribonucleic acid) sequences, amino-acid sequences, and audio and video sequences that are preprocessed into a discrete symbolic form.

More specifically, the present invention realizes that, in common linguistic usage, people typically convey information in highly stereotyped ways. So, for example, in a phone call, the caller is likely to identify himself in one of just a few ways, e.g., "Hi <recipient-name>, it's <caller-name>" (e.g., "Hi John, it's Bob") or "<recipient-name>, <caller-name> here" (e.g., "John, Bob here"). Or in a cover letter, a job applicant is likely to express his interest with a phrase like "I am looking for a job in <field>" (e.g., "I am looking for a job in electrical engineering").

In accordance with this realization, the present invention provides techniques for enumerating regularly identifiable or stereotypical phrases that people commonly use to convey particular information, and where exactly in these phrases the particular information is to be found. In one embodiment, such phrases are referred to as "regular expressions." Using such enumerated phrases, the invention is able to automatically identify them in an input data stream and then identify and extract the particular information associated with the phrase that is being sought, e.g., important or relevant information.

This approach has several advantages over the previously mentioned tagging approach. First, the phrases are readily expressible as regular expressions, and this allows them to be stored in one of several common programming languages, e.g., as a "flex" or "perl" program. Both these languages have built-in support for regular expressions. Secondly, the use of regular-expression technology enables extremely fast pattern matching and information extraction with highly optimized standard programs. Thirdly, the phrases can be identified without the expensive and time consuming step of gathering and annotating a large "training" database. Finally, if desired, the technique can be combined with statistical based procedures, e.g., by using the phrases as features in a statistical system, or by using a statistical procedure to automatically collect a large pool of candidate phrases which can then be selected for inclusion by a human.

One skilled in the art will realize various applications for the invention. By way of example only, such enumerated phrases may be automatically identified in a transcribed voice mail message, and the important information in the message, e.g., a phone number or caller's name, may be automatically extracted and presented to the user or stored for subsequent use.

These and other objects, features and advantages of the present invention will become apparent from the following detailed description of illustrative embodiments thereof, which is to be read in connection with the accompanying drawings.

DETAILED DESCRIPTION OF PREFERRED EMBODIMENTS

As will be explained in detail below, the present invention provides techniques for using stereotypical phrases or "regular expressions" to identify the information-bearing portions of a document, and thereby explicitly identity the information found therein. Regular expressions, as have been discussed in Aho et al., "Compilers: Principles, Techniques, and Tools," Addison-Wesley, 1985, the disclosure of which is incorporated by reference herein, comprise symbolic strings, typically word sequences, that can be constructed by the basic operations of "and" and "or" acting on an atomic alphabet of symbols. So, for example, the pattern "the dog" produces a match only when, in the data being considered, the symbol "the" is followed by the symbol "dog." This represents the operation of concatenation or "and." The pattern "the (dog|cat)" illustrates the "or" operation, i.e., the pattern matches either the string "the dog" or "the cat." The operation of "classing" is also possible. So, for example, a "pet" class may be defined as either "dog" or "cat:"

<animal>::=(dog|cat)

Then, subsequent regular expressions can make use of this class, for example, the pattern: "the <pet>." A wide variety of extensions to regular expressions exist, for example, restrictions on where in a document a pattern is found, or restrictions on the length of repeated sequences in a regular expression. In accordance with an illustrative embodiment of the invention, the term "regular expression" is taken to mean any form of pattern that is matchable in the flex, lex, or perl programming languages, although the invention is not limited thereto. The programming languages flex and lex are described in J. R. Levine et al., "Lex & Yacc," 1992, the disclosure of which is incorporated by reference herein. The programming language perl is described in L. Wall et al., "Programming Perl," 1996, the disclosure of which is incorporated by reference herein. Similarly, in accordance with such an illustrative embodiment, the term "matching" refers to the processes by which these programs match their input.

In accordance with an embodiment of the invention, when an information-bearing regular expression is matched, an action is taken to present the information in an appropriate way. There are two main types of regular expressions that may be used in this particular embodiment: trigger prefixes and trigger suffixes.

A trigger prefix is a characteristic phrase that typically precedes a piece of information, for example, in a voice mail message, "give me a call back at" is a trigger phrase that precedes a phone number.

A trigger suffix is a phrase that typically follows a key piece of information, even when a trigger prefix is not present. For example, the phrase "talk to you later bye" is often a post-facto signal that a phone number has been provided, when the words immediately preceding the phrase are a sequence of numbers.

In this embodiment of the invention, trigger prefixes and suffixes may be used either separately, or combined together into larger composite patterns. The operation of word classing is also inherent in this embodiment of the invention. For example, a set of personal names such as those found in a phone book may be identified a a "person-name" class. Subsequently, patterns of the form "Hi, it's <person-name>+" can be matched, and the words matching the "person-name" tokens can be displayed as the caller. It is to be understood by those skilled in the art that there are numerous ways of combining trigger prefixes and suffixes, word classes, and other pattern-matching operations, such as the use of multiple states, each with its own set of matchable patterns (as may be done in flex) in order to identify and extract information.

In addition to being used as a stand-alone method for information extraction, regular expressions can be in combination with statistical techniques. For example, the existence of a pattern such as "Hi <person-name>, it's <person-name>" can be used as a feature in a maximum-entropy word-tagging system.

Figure 1:
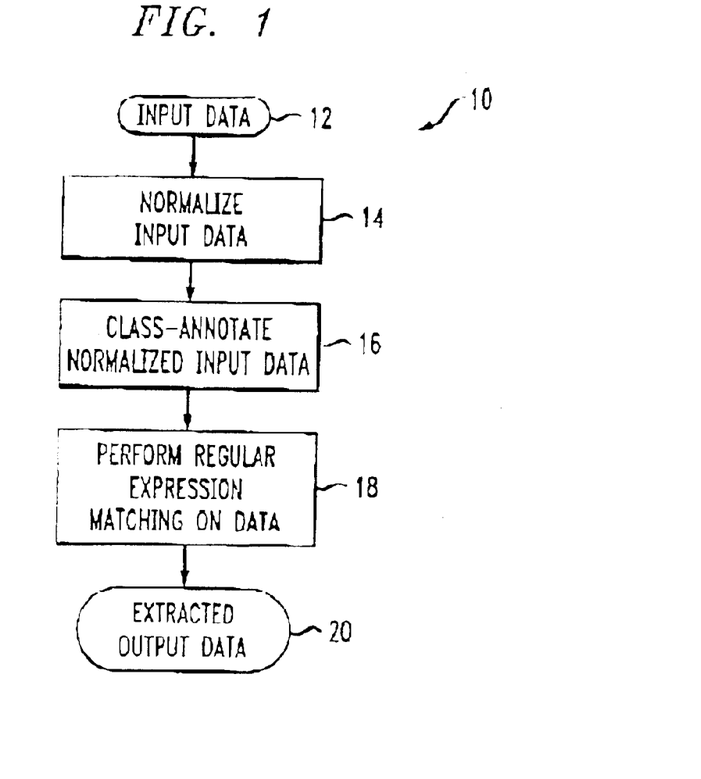
FIG. 1 is a flow diagram illustrating an information extraction methodology according to an embodiment of the present invention.

Referring now to FIG. 1, a flow diagram illustrates an information extraction methodology according to an embodiment of the present invention. As shown in FIG. 1, the methodology 10 begins by obtaining the input data 12 to be processed. As mentioned above, the input data is a sequence of discrete symbols or a document, such as may be representative of text and/or a transcribed spoken message.

In step 14, the input data is normalized. This process may include standardizing any characteristics of the input that are irrelevant to, or a hindrance to, information extraction. An example of normalization, for text input, is to change all the letters in the text stream to lower-case and to replace multiple blank spaces between words by a single blank space. This makes subsequent pattern matching easier.

By way of example, the following is a sample flex program for normalizing text input:

```
%{
#include <iostream.h>
#include <ctype.h>
%}
%option noyywrap
%option never-interactive
ws [\t]+
%%
-                           {cout <<"";}
[!\.@,"()?]                 {;}
\<[ \>]*\>{ws}*             {;}
{ws}                        {cout<<"";}
.                           {cout<<char(tolower(*yytext));}
%%
main()
{
        yylex();
}
```

In step 16, one or more previously-stored word (or, in general, one or more symbols) lists are used to identify and mark occurrences of words that belong to certain classes. By way of example, such a class-annotation operation may include marking all proper names by prefixing them with an "!" mark.

By way of example, the following is a sample C++ program for annotating names identified in a normalized text stream:

```
#include <iostream.h>
#include <fstream.h>
#include <stdlib.h>
#include <set>
include <string>
main()
{
    set<string>name;
    ifstream namesin("../data/person_names"); // a text file listing names
    if (!namesin)
    {
        cout << "Unable to find ../data/person_names\n";
        exit(1);
    }
    while (!namesin.eof())
    {
        string s;
        namesin>>s>>ws;
        name.insert(s);
```

```
    }
    namesin.close();
    while (!cin.eof())
    {
        string s;
        cin>>s>>ws;
        if (name.count(s))
            cout<<"!"<<s<<"";
        else
            cout<<s<<"";
    }
}
```

In step 18, the normalized and class-annotated text is read by a regular-expression matching program, and the information-bearing portions of the text are analyzed and extracted. In a preferred embodiment, the regular expressions are specified in and matched by a specialized regular expression matching program, such as may be implemented in flex. In this process, it is understood that all the mechanisms available in such a programming language may be used. These include the use of special start states, backtracking, context-sensitive matching, and embedded special-purpose "C" code.

Specifically, the matching operation in step 18 takes the normalized, class-annotated input data and identifies the regular expressions in the data by comparing the data to previously-stored regular expressions. These previously-stored regular expressions may include, for example, trigger prefixes, trigger suffixes, word classes, and other matchable patterns. When a match occurs, the structure of the regular expression is analyzed to identify the information-bearing portion of the expression. The information is then extracted from the expression.

By way of example, the following is a sample flex program for identifying caller names and phone numbers in a transcribed voice mail messages. As is evident, the program enumerates a plurality of regular expressions, categorized as

```
PHONE_NUMBER_STATE, NAME_STATE, EXTENDED_NAME_STATE, and
TERMINATION_STATE, that are considered during matching step 18:
%{
#include< iostream.h>
#include< string.h>
const char *number_type;
const char *t1 = "tieline";
const char *extension = "extension";
const char *pager = pager";
const char *fax = "fax number";
const char *none = " ";
char number_buff[10000];
%}
%option noyywrap
%option never-interactive
/* many patterns like IN-GENERIC_NAME-AT-DIGIT+unaccounted for */
spelled_digit
((zero | one | oh | two | three | four | five | six | seven | eight | nine | hundred | thousand | ten |
eleven | twelve | thirteen | fourteen | fifteen | sixteen | seventeen | eighteen | nineteen | twenty |
thirty | forty | fifty | sixty | seventy | eighty | ninety | hundred) [ ]?)
numeric_digit ((1 | 2 | 3 | 4 | 5 | 6 | 7 | 8 | 9 | 10) [ ]?)
digit ([ ]?{spelled_digit} | [ ]?{numeric_digit})
phone_number ((country[ ]code[ ] {digit} {2,})?(toll[ ]free)?(area[ ] | area[ ]code[ ])?
{digit}{2,}((or[ ] | tha's [ ] | sorry [ ]) | {digit} {2,})?(option[ ] {digit}+)?(extension[ ]
{digit}{2,})?) tie_line ([ ]?(tie[ ]line | tieline) ([ ]number)?)
name ![a-z']+
%x PHONE_NUMBER_STATE
%x NAME_STATE
%x EXTENDED_NAME_STATE
%x TERMINATION_STATE
%%
(1 | 2 | 3 | 4 | 5 | 6 | 7 | 8 | 9 | 0)+ ":" {cout << yytext << endl; /* get header */}
{digit}({digit} | "extension"){3,} {strcpy(number_buff, yytext); BEGIN
TERMINATION_STATE;}
<TERMINATION_STATE>"thank you" |
<TERMINATION_STATE>"thanks" |
<TERMINATION_STATE>"take care" |
<TERMINATION_STATE>"bye" |
<TERMINATION_STATE>"talk to you" |
<TERMINATION_STATE>"okay bye" |
<TERMINATION_STATE>"have a "(good | great)" day" {cout << "Number: "
<<number_buff<<endl; BEGIN INITIAL;}
<TERMINATION_STATE><<EOF>> {cout << "Number: "number_buff << endl;
BEGIN INITIAL;}
<TERMINATION_STATE>.{unput(*yytext); BEGIN INITIAL;}
"on extension" |
"at extension" |
"extension" |
"extension is" {number_type = extension; BEGIN PHONE_NUMBER_STATE;}
"my "{tie_line}" is" |
"my "{tie_line}" here is" |
{tie_line}"is" |
"{tie_line}" " {number_type = tl; BEGIN PHONE_NUMBER_STATE;}
```

```
"again is" |
"again" |
"back" |
"call me |
"call me at" |
"call me back at" |
"call me "[a-zA-Z]+"at" |
"call me back on" |
"call me on" |
"call back at" |
"call back on" |
"give me a buzz" |
"give me a buzz at" |
"give me a holler" |
"give me a holler at" |
"give me a ring" |
"give me a call" |
"give me a ring at" |
"give me a call at" |
"give me a call at home" |
"give me a call at work" |
"give me a call at your convenience" |
"give me a call back at" |
"give me a call back on" |
"give me a call back with that information at" |
"give me a call if you get a chance" |
"give me a call please" |
"give me a call please at" |
"give me a call when you get a chance" |
"give me a call when you can" |
"give me a call when you can please" |
"give us a call" |
"give us a call at" |
"here" |
"i can be reached at" |
"i am at" |
"i'm at" |
"i'll be at" |
"i'm on" |
"leave me a message" |
"leave me a message at" |
"my number is" |
"my number here is" |
"my number here in "(!?[a-z]+[ ])"is" |
"my number's" |
"my phone number's" |
"number again is" |
"number at home is" |
"number at work is" |
"number here is" |
"number is" |
"number's" |
"number at work is" |
"outside line" |
"outside" |
"please call" |
"phone" |
"please return our call at" |
"reach met at" |
"returning your call" |
"talk to you later" |
"try me at" |
"try me at this number" |
"you could reach us at" |
"when you have a chance" |
"when you get a chance" {number_type=none; BEGIN PHONE_NUMBER_STATE;}
"fax number is" |
"my fax number's " {number_type=fax; BEGIN PHONE_NUMBER_STATE;}
"my pager" |
"my pager is" |
"give me a page" |
"give me a page at" |
"page me at" |
"page me" |
"page number" {number_type=pager; BEGIN PHONE_NUMBER_STATE;}
<PHONE_NUMBER_STATE>{phone_number} {cout << "Number:" << number_type
  << yytext << endl; BEGIN INITIAL;}
<PHONE_NUMBER_STATE>.{unput(*yytext); BEGIN INITIAL;}
"it's"{phone_number } |
```

-continued

```
"on "{phone_number } {char *c=strchr(yytext, ' '); c++; cout << "Number: " << c <<endl;}
"it's me" |
"it's just me" {cout << "Name: me" << endl;}
"this is your wife" {cout << "Name: wife" << endl;}
"this is receiving" {cout << "Name: receiving" << endl;}
"this is the mail room" {cout << "Name: the mail room" << endl;}
  ^({name}[ ]){2,3} {cout << "Name: " << (strchr(yytext, ' ')+1) << endl;}
("hi" | "hey" | "hello") {name}" "{name}" "{name}" ")? {char *c=strchr(yytext, ' ';)
c=strchr(c+1, ' '); cout << "Name: " << (c+1) << endl;}
"good morning" {name}" " |
"yeah" {name}" " |
({name} [ ])? "this is" |
{name}"it's" |
{name}"hi" |
"hi i'm" |
"my name is" |
"my name's" |
"the name is" |
"the name's" |
"hey"({name}[ ])? "this"("is")? |
"hi"({name}[ ])? "this"("is")? |
({name}[ ])? "hi it's" |
({name}[ ])? "hey it's" |
({name}[ ])? "how you doing it's" |
{name}"this"   }BEGIN NAME_STATE;}
<NAME_STATE>({name}[ ])+ {cout << "Name: " << yytext << endl;
number_type=none;
BEGIN PHONE_NUMBER_STATE;}
<NAME_STATE>("me" | "mom" | "your sis" | "your sister" | "your wife" | "your brother" |
"your father" | "your husband") {cout << "Name: " << yytext << endl; BEGIN INITIAL;}
<NAME_STATE>({name}[ ])+"from" |
<NAME_STATE>({name}[ ])+"calling from" |
<NAME_STATE>({name}[ ])+"i'm calling from" |
<NAME_STATE>({name}[ ])+"with" |
<NAME_STATE>({name}[ ])+"i'm with" |
<NAME_STATE>({name}[ ])+"at" |
<NAME_STATE>({name}[ ])+"over at" |
<NAME_STATE>({name}[ ])+"down at" |
<NAME_STATE>({name}[ ])+"over in" |
<NAME_STATE>({name}[ ])+"up in" |
<NAME_STATE>({name}[ ])+"down in" |
<NAME_STATE>({name}[ ])+"up on" |
<NAME_STATE>({name}[ ])+"down on" |
<NAME_STATE>({name}[ ])+"in" {cout << "Name: " << yytext; BEGIN EXTENDED_NAME_STATE;}
<NAME_STATE>. {unput(*yytext); BEGIN INITIAL;}
<EXTENDED_NAME_STATE>"i'm" |
<EXTENDED_NAME_STATE>"i" |
<EXTENDED_NAME_STATE>"i've" |
<EXTENDED_NAME_STATE>"i'd" |
<EXTENDED_NAME_STATE>"my" |
<EXTENDED_NAME_STATE>"it's" |
<EXTENDED_NAME_STATE>"it is" |
<EXTENDED_NAME_STATE>"we" |
<EXTENDED_NAME_STATE>"when" |
<EXTENDED_NAME_STATE>"you" |
<EXTENDED_NAME_STATE>"calling" |
<EXTENDED_NAME_STATE>"now" |
<EXTENDED_NAME_STATE>"a" |
<EXTENDED_NAME_STATE>"if" |
<EXTENDED_NAME_STATE>"give" |
<EXTENDED_NAME_STATE>"their" |
<EXTENDED_NAME_STATE>"and" |
<EXTENDED_NAME_STATE>"notifying" |
<EXTENDED_NAME_STATE>"returning" |
<EXTENDED_NAME_STATE>"sorry" |
<EXTENDED_NAME_STATE>"can" |
<EXTENDED_NAME_STATE>"got" |
<EXTENDED_NAME_STATE>"earlier" |
<EXTENDED_NAME_STATE>"your" |
<EXTENDED_NAME_STATE>"just" |
<EXTENDED_NAME_STATE>"that" |
<EXTENDED_NAME_STATE>"could" |
<EXTENDED_NAME_STATE>"would" |
<EXTENDED_NAME_STATE>"before" |
<EXTENDED_NAME_STATE>"thanks" |
<EXTENDED_NAME_STATE>"thank" |
<EXTENDED_NAME_STATE>"wanted" |
<EXTENDED_NAME_STATE>"following" |
<EXTENDED_NAME_STATE>"regarding" |
```

-continued

```
<EXTENDED_NAME_STATE>"may" |
<EXTENDED_NAME_STATE>"let" |
<EXTENDED_NAME_STATE>"he" |
<EXTENDED_NAME_STATE>"about" |
<EXTENDED_NAME_STATE>"again" |
<EXTENDED_NAME_STATE>"wanting" |
<EXTENDED_NAME_STATE>"appreciate" |
<EXTENDED_NAME_STATE>"was" |
<EXTENDED_NAME_STATE>"we're" |
<EXTENDED_NAME_STATE>"or" |
<EXTENDED_NAME_STATE>"you've" |
<EXTENDED_NAME_STATE>"right" |
<EXTENDED_NAME_STATE>"first" |
<EXTENDED_NAME_STATE>[ ]?"tieline" |
<EXTENDED_NAME_STATE>[ ]?"extension" |
<EXTENDED_NAME_STATE>" " {digit} |
<EXTENDED_NAME_STATE>"please" {cout << endl; char *q=yytext+strlen(yytext);
while (q>yytext) unput(*--q); number_type=none; BEGIN PHONE_NUMBER_STATE;}
<EXTENDED_NAME_STATE>. {ECHO;}
.{;}
%%
main( )
{
    yylex( );
    cout << endl;
}
```

Thus, by way of example, if the voice message input to the methodology 10 contains the phrase "call me back at 555–1234," the above program determines that the phrase "call me back at" matches one of the enumerated expressions. Then, the information associated with the phrase "call me back at," namely, "555–1234," is identified as the information-bearing portion of the expression, and extracted.

The extracted output data 20 may then be presented to a user. For example, this may include displaying the information to the user on a display or converting the information to audio and audibly presenting the information to the user in accordance with an output speaker. The extracted data may also be used to take some other specified action, e.g., place extracted data in an electronic phone book, notify user of a message from a particularly important person, notify a user of a message on a particular topic, etc.

Figure 2:
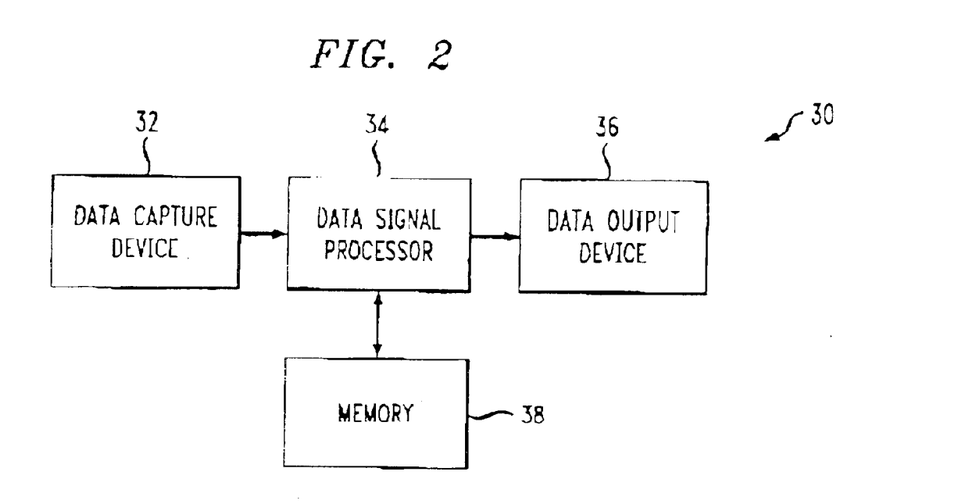
FIG. 2 is a block diagram illustrating a generalized hardware architecture of a data processing system suitable for implementing an information extraction methodology according to the present invention.

Referring now to FIG. 2, a block diagram illustrates a generalized hardware architecture of a data processing system suitable for implementing an information extraction methodology according to the present invention. As shown, the system 30 includes a data capture device 32, a data signal processor 34, a data output device 36, and memory 38.

The data capture device 32 generally obtains the data stream that is to be processed by the system 30. The device's specific structure and operations depend on the application in which the system is employed. For example, in a voice mail application, the data capture device may be a speech processing device capable of taking an audio stream recorded in accordance with a voice mail system and converting or transcribing the audio stream to a discrete data or symbol sequence. The device may, for example, utilize conventional speech recognition techniques or some other known transcription techniques. In a text based application, the device may be a digital scanner capable of converting a text document into a discrete data or symbol sequence. The device may, for example, utilize conventional optical character recognition techniques. Of course, depending on the data type, the data capture device may take on alternate forms.

The data signal processor 34 generally performs and/or controls the operations of the methodologies of the present invention, in conjunction with the memory 38. That is, the signal processor performs and/or controls the steps depicted in the flow diagram of FIG. 1.

It is to be appreciated that the term "processor" as used herein is intended to include any processing device, such as, for example, one that includes a CPU (central processing unit) or other processing circuitry. For example, the processor may be a digital signal processor, as is known in the art. Also the term "processor" may refer to one or more individual processors. The term "memory" as used herein is intended to include any memory devices associated with a processor or CPU, such as, for example, RAM, ROM, a fixed memory device (e.g., hard drive), a removable memory device (e.g., diskette), flash memory, etc. It is to be understood that the previously-generated word classes and regular expressions used in the class-annotation and expression matching operations, described above in accordance with the invention, may be stored in memory 38 and accessed when required.

Accordingly, one or more computer software programs including instructions or code for performing the methodologies of the invention, as described herein, may be stored in one or more of the associated memory devices (e.g., ROM, fixed or removable memory) and, when ready to be utilized, loaded in part or in whole (e.g., into RAM) and executed by a CPU.

The data output device 36 generally presents the data extracted from the input data stream to a user. Again, the device's specific structure and operations depend on the application in which the system is employed. For example, in a voice mail application, the data capture device may be an audio output system capable of taking the extracted discrete data and converting the data to a form to be audibly output to the user. The device may, for example, utilize conventional text-to-speech or other speech synthesis techniques. Such techniques may also be used in a text based application. Alternatively, the device may be a display for visually presenting the extracted data to the user. Of course, depending on the data type, the data output device may take on alternate forms.

It is to be understood that the elements illustrated in the figures may be implemented in various forms of hardware, software, or combinations thereof, e.g., one or more digital signal processors with associated memory, application specific integrated circuit(s), functional circuitry, one or more appropriately programmed general purpose digital computers with associated memory, etc. For example, the information extraction methodologies of the invention may be implemented in various personal computing devices. Given the teachings of the invention provided herein, one of ordinary skill in the related art will be able to contemplate other implementations of the elements of the invention.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method of automatically processing an input sequence of data symbols, the method comprising the steps of:
   identifying at least one regularly identifiable expression in the input sequence of data symbols, wherein the at least one regularly identifiable expression represents a pattern that is matchable in accordance with a programming language that supports such a regularly identifiable expression;
   identifying at least a portion of information associated with the at least one regularly identifiable expression; and
   extracting the portion of information.

2. The method of claim 1, wherein the regularly identifiable expression identifying step comprises comparing the input sequence of data symbols to one or more previously-stored regularly identifiable expressions to determine if there is a match between a portion of the input sequence and at least one of the previously-stored regularly identifiable expressions.

3. The method of claim 1, further comprising the step of normalizing the input sequence of data symbols prior to identifying the regularly identifiable expression.

4. The method of claim 1, further comprising the step of identifying one or more classes of data symbols in the input sequence prior to identifying the regularly identifiable expression.

5. The method of claim 1, wherein the at least one regularly identifiable expression comprises a characteristic phrase that typically precedes a particular portion of information.

6. The method of claim 1, wherein the at least one regularly identifiable expression comprises a characteristic phrase that typically follows a particular portion of information.

7. The method of claim 1, wherein the extracted portion of information is used to take a specified action.

8. The method of claim 1, wherein the extracted portion of information is at least one of visually and audibly presented to the user.

9. The method of claim 1, wherein the regularly identifiable expression identifying step is performed in accordance with one or more programs written in one of the flex, lex, and perl programming language.

10. The method of claim 1, wherein the input sequence of data symbols is representative of at least one of text data, transcribed spoken data, deoxyribonucleic acid sequence data, ribonucleic acid sequence data, amino-acid sequence data, audio sequence data, and video sequence data.

11. The method of claim 1, wherein the input sequence of data symbols is representative of a voice mail message.

12. Apparatus for automatically processing an input sequence of data symbols, the apparatus comprising:
    at least one processor operative to: (i) identify at least one regularly identifiable expression in the input sequence of data symbols, wherein the at least one regularly identifiable expression represents a pattern that is matchable in accordance with a programming language that supports such a regularly identifiable expression; (ii) identify at least a portion of information associated with the at least one regularly identifiable expression; and (iii) extract the portion of information; and
    memory, operatively coupled to the at least one processor, for storing at least a portion of results associated with the identifying and extracting operations.

13. The apparatus of claim 12, wherein the regularly identifiable expression identifying operation comprises comparing the input sequence of data symbols to one or more regularly identifiable expressions, previously stored in the memory, to determine if there is a match between a portion of the input sequence and at least one of the previously-stored regularly identifiable expressions.

14. The apparatus of claim 12, wherein the at least one processor is further operative to normalize the input sequence of data symbols prior to identifying the regularly identifiable expression.

15. The apparatus of claim 12, wherein the at least one processor is further operative to identify one or more classes of data symbols in the input sequence prior to identifying the regularly identifiable expression.

16. The apparatus of claim 12, wherein the at least one regularly identifiable expression comprises a characteristic phrase that typically precedes a particular portion of information.

17. The apparatus of claim 12, wherein the at least one regularly identifiable expression comprises a characteristic phrase that typically follows a particular portion of information.

18. The apparatus of claim 12, wherein the extracted portion of information is used to take a specified action.

19. The apparatus of claim 12, wherein the extracted portion of information is at least one of visually and audibly presented to the user.

20. The apparatus of claim 12, wherein the regularly identifiable expression identifying operation is performed in accordance with one or more programs written in one of the flex, lex, and pen programming language.

21. The apparatus of claim 12, wherein the input sequence of data symbols is representative of at least one of text data, transcribed spoken data, deoxyribonucleic acid sequence data, ribonucleic acid sequence data, amino-acid sequence data, audio sequence data, and video sequence data.

22. The apparatus of claim 12, wherein the input sequence of data symbols is representative of a voice mail message.

23. An article of manufacture for use in automatically processing an input sequence of data symbols, comprising a machine readable medium containing one or more programs which when executed implement the steps of:
    identifying at least one regularly identifiable expression in the input sequence of data symbols, wherein the at least one regularly identifiable expression represents a pattern that is matchable in accordance with a programming language that supports such a regularly identifiable expression;
    identifying at least a portion of information associated with the at least one regularly identifiable expression; and
    extracting the portion of information.

24. Apparatus for automatically processing an input sequence of data symbols, the apparatus comprising:
- a data capture device for obtaining the input sequence of data symbols;
- at least one processor, operatively coupled to the data capture device, operative to: (i) identify at least one regularly identifiable expression in the input sequence of data symbols. wherein the at least one regularly identifiable expression represents a pattern that is matchable in accordance with a programming language that supports such a regularly identifiable expression; (ii) identify at least a portion of information associated with the at least one regular expression; and (iii) extract the portion of information;
- memory, operatively coupled to the at least one processor, for storing at least a portion of results associated with the identifying and extracting operations; and
- a data output device, operatively coupled to the at least one processor, for presenting the extracted portion of information to a user.

25. A method of automatically processing an input document, the method comprising the steps of:
- identifying one or more regular expressions in the input document by comparing the input document to one or more previously-stored regular expressions to determine if there is a match between a portion of the input document and at least one of the previously-stored regular expressions, wherein a regular expression represents a pattern that is matchable in accordance with a programming language that supports such a regular expression; and
- identifying at least a portion of information associated with the at least one regular expression for extraction.

* * * * *

EX PARTE REEXAMINATION CERTIFICATE (12829th)

United States Patent
Zweig et al.

(10) Number: US 6,842,796 C1
(45) Certificate Issued: Jan. 29, 2025

(54) INFORMATION EXTRACTION FROM DOCUMENTS WITH REGULAR EXPRESSION MATCHING

(75) Inventors: Geoffrey G. Zweig, Greenwich, CT (US); Mukund Padmanabhan, White Plains, NY (US)

(73) Assignee: TAASERA LICENSING LLC, Marshall, TX (US)

Reexamination Request:
No. 90/015,326, Nov. 6, 2023

Reexamination Certificate for:
Patent No.: 6,842,796
Issued: Jan. 11, 2005
Appl. No.: 09/898,289
Filed: Jul. 3, 2001

(51) Int. Cl.
*G10L 15/00* (2013.01)
*G06F 40/20* (2020.01)
*G06F 40/289* (2020.01)
*G10L 15/08* (2006.01)

(52) U.S. Cl.
CPC ............ *G06F 40/20* (2020.01); *G06F 40/289* (2020.01); *G10L 2015/088* (2013.01); *Y10S 707/99931* (2013.01); *Y10S 707/99936* (2013.01)

(58) Field of Classification Search
None
See application file for complete search history.

(56) References Cited

To view the complete listing of prior art documents cited during the proceeding for Reexamination Control Number 90/015,326, please refer to the USPTO's Patent Electronic System.

*Primary Examiner* — B. James Peikari (57) ABSTRACT

Techniques are provided for enumerating regularly identifiable or stereotypical phrases that people commonly use to convey particular information, and where exactly in these phrases the particular information is to be found. In one embodiment, such phrases are referred to as "regular expressions." Using such enumerated phrases, the invention is able to automatically identify them in an input data stream and then identify and extract the particular information associated with the phrase that is being sought, e.g., important or relevant information.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-25 are cancelled.

* * * * *